United States Patent [19]

Becker et al.

[11] Patent Number: 5,177,258
[45] Date of Patent: Jan. 5, 1993

[54] METHOD OF PRODUCTION OF BIARYL DERIVATIVES

[75] Inventors: Abram Becker, Paris, France; Ariel A. Ewenson, Omer; Bertha Croitoru, Beer-Sheva, both of Israel

[73] Assignee: Bromine Compounds, Ltd., Beer-Sheva, Israel

[21] Appl. No.: 887,344

[22] Filed: May 21, 1992

[30] Foreign Application Priority Data

May 22, 1991 [IL] Israel .......................................... 98209

[51] Int. Cl.$^5$ .................... C07C 51/347; C07C 39/15; C07C 206/06
[52] U.S. Cl. ..................................... 562/488; 562/469; 562/492; 568/450; 568/730; 568/747; 568/707; 568/636; 568/638; 568/717; 568/931
[58] Field of Search ....................... 562/488, 469, 492; 568/730, 747, 717, 433, 435, 707, 636, 638, 931

[56] References Cited

U.S. PATENT DOCUMENTS 4,727,185  2/1988  Shoji et al. .......................... 562/488

FOREIGN PATENT DOCUMENTS 0409172  1/1991  European Pat. Off. ............ 562/488
2026238  2/1987  Japan ................................... 562/488

Primary Examiner—Marianne M. Cintins
Assistant Examiner—Margaret J. Argo
Attorney, Agent, or Firm—Michael N. Meller

[57] ABSTRACT

Biaryl derivatives are produced by coupling an aryl halide in an aqueous alkaline solution in the presence of a palladium catalyst, using formic hydrazide as the reducing agent.

20 Claims, No Drawings

METHOD OF PRODUCTION OF BIARYL DERIVATIVES

FIELD OF THE INVENTION

The present invention relates to an improved method of production of biaryl derivatives by the reductive coupling of aryl halide compounds.

BACKGROUND OF THE INVENTION

Functional biaryl derivatives are important inductrial chemicals. They are used in the production of monomers for high performance and other polymers. For example, 3,3',4,4'-biphenyltetracarboxylic acid (BPTC), 4,4'-biphenyldicarboxylic acid and 4,4'-biphenol are monomers used in the manufacture of high performance polyimides, polyamides and polyesters. In addition, the biaryl derivatives are useful in the production of dyes, pharmaceuticals and agrochemical intermediates. These applications require very high purity (often above 99.9%) of the biaryl derivatives.

THE PRIOR ART

The conventional production processes for biaryls by the reductive coupling of aryl halides involve the following general components:
1. A liquid medium such as methanol, ethanol, dioxane, glycols, $H_2O$, etc.
2. A base such as NaOH, KOH.
3. A metallic catalyst such as Pd, Rh, Ru, Ni.
4. A reducing agent such as sodium formate, paraformaldehyde, glycols, glycerol, methanol, chloroform/methylamine, hydrazine, CO, $H_2$.

For example, Busch et al., Ber. (1929) 62, 2612 and Busch et al., J. Prakt. Chem. (1936) 146 describe the coupling of aryl halides in alcoholic KOH in the presence of $Pd/CaCO_3$ as catalyst, with hydrogen or hydrazine as reducing agent, by warming the reaction mixture to reflux or under pressure to higher temperatures. This coupling method generally gives fair yields of biphenyl derivatives with simple aryl halides. For example, bromobenzene gave ca. 78% biphenyl and p-bromotoluene gave ca. 66% 4,4'-dimethylbiphenyl.

However, Busch et al. found that with aromatic compounds containing polar substituents, the selectivity to biphenyls was much lower. For example, p-bromophenol gave ca. 13.4% 4,4'-dihydroxybiphenyl, p-bromoanisole gave ca. 35% 4,4'-dimethoxybiphenyl, bromobenzoic acid gave 40% 4,4'-biphenyldicarboxylic acid and 3-bromobenzoic acid gave 56.5% 3,3'-biphenyldicarboxylic acid.

Several patents also describe reductive coupling processes for aryl halides. For example, Japanese Patent No. 0253742 describes the reductive coupling of chlorophthalic acid with Pd/C in aqueous NaOH with glycerol as the reducing agent, to give 53-64% of BPTC (the rest is phthalic acid) by warming at 150° C. at 2 $kg/cm^2$.

JP 01,224,330 describes the reductive coupling of monosodium chlorophthalate in water, using Pd/C in the presence of chloroform and monomethylamine at 120° C. and 5 $kg/cm^2$ to give 74% BPTC and 26% of phthalic acid.

JP 01,299,236 describes a reductive coupling of chlorophthalic acid in aqueous NaOH, using Pd/C, glycerine and hydrogen at 150° C. and 9.5 $kg/cm^2$ for 5 hours to give 64.5% BPTC and 35.5% phthalic acid. The reused catalyst gave the reduced yield of 49.8% BPTC at 84.8% conversion.

JP 62/026238 discloses the reductive coupling of chlorophthalic acid in aqueous NaOH with 2% Pd/C in an amount of about 11% by weight based on the chlorophthalic acid used in conjunction with the following reducing agents: ethylene glycol, 28-42% yield of BPTC; methanol, 36.6% yield; glycerine, 50.3% yield (100% conversion); and paraformaldehyde, 38% yield and 100% conversion.

JP 61/137838 describes a reductive coupling of a sodium salt of 4-bromophthalic acid using ~25% by weight of 5% Pd/C, 50% by weight of KOH and 30% by weight of sodium formate, based on BPTC produced in water at 100° C. for 6 hours to give 92% of BPTC.

These methods of reductive coupling of halophthalic acids to produce BPTC present several problems:
(a) All the reducing agents used, except sodium formate, give only low to moderate yields of BPTC (24-72%). In the case of sodium formate, a large amount of catalyst is necessary: up to 25% by weight of 5% Pd/C, based on the obtained BPTC, was used to get a yield of 92%.
(b) The expensive palladium catalyst must be recovered. Usually the selectivity and reaction rates using recycled catalyst were found to be greatly reduced, and a regeneration treatment was necessary to restore at least part of its activity. Complete recovery of the total activity has not been reported. This renders the turnover number too low, and the cost of catalyst prohibitive.
(c) The amount of reducing agent used is quite important. Sodium formate is used in equal weight with respect to the BPTC obtained. Ethylene glycol is used to the extent of up to 3 parts to one part of BPTC; methanol, up to 10 parts of BPTC; and glycerol, about 5 parts. These amounts are quite large. In the case of sodium formate glycol and glycerol, product recovery is quite tedious and expensive. These processes, therefore, are characterized by low throughputs and present ecological problems.
(d) The purification of the BPTC obtained is quite difficult unless high conversion and selectivity are obtained.

For example, it has been found that in the synthesis of BPTC, if the conversion is lower than 100% and selectivity is lower than 75%, extensive purification is needed in order to obtain BPTC with a purity of over 99%, which is the minimum purity required for the polycondensation process for which this material is used. Impurities such as phthalic acid and unreacted 4-halophthalic acid are chain stoppers in the above-mentioned polymerization process, yielding low-grade polymers.

SUMMARY OF THE INVENTION

It has now been found, and this is an object of the present invention, that all the above-mentioned problems can be overcome by a simple and economic process.

The process according to the invention comprises coupling an aryl halide to give a biaryl derivative, using a palladium catalyst in a small amount, which can be recovered and recycled, substantially without losing its selectivity or its reactivity, in an aqueous alkali medium, using formic hydrazide as the reducing agent. The process of the invention yields biaryl derivatives in high selectivity and yields.

Illustrative, but non-limitative examples of aryl halides are 1-chloro-2-nitrobenzene, 1-chloro-4-nitrobenzene, 1-bromo-2-nitrobenzene, 1-bromo-4-nitrobenzene, 4-bromobenzaldehyde, 5-bromosalicyclic acid, 5-bromoanthranilic acid, 4-bromobiphenyl, 4-bromophenoxybenzoic acid.

According to the present invention, an aryl halide is stirred in an aqueous alkaline medium such as NaOH. The amount of alkali used is enough to neutralize the hydrogen halide liberated, in addition to that required to neutralize other acidic groups which may be present, such as carboxylic and/or phenolic groups. Usually an excess of alkali is added (up to 50%).

The amount of palladium catalyst (for a 5% Pd/C) needed to give high selectivities is between 0.04 to 4% of the weight of the aryl halide used, preferably from 0.08 to 1%. Of course, different catalyst batches, supports and Pd contents may require different catalytic amounts, the determination of which is within the skill of the routine practitioner. The molar amount of formic hydrazide needed with respect to the halide is approximately 1:4, respectively.

The reaction is performed at a temperature between 60° to 100° C., preferably between 60° to 85°. 100% Conversion is obtained after 15 to 90 minutes of warming, depending on the nature of the aryl halide and the amount of catalyst used. It has been found that heating the reaction mixture for longer periods of time does not bring about catalyst deterioration.

The selectivity of the reductive coupling is high and biphenyl derivatives are formed to an extent usually of 80 to 90% and in some cases even 95%. For example, using formic hydrazide, 4-bromophthalic acid gives >90% BPTC at 100% conversion when 0.08% of 5% Pd/C was used at a temperature of 80° C. for 90 minutes. It has surprisingly been found that the recovered catalyst can be reused for several cycles after a simple washing, substantially without loss of selectivity or reactivity.

The efficiency of formic hydrazide in producing biphenyl derivatives is quite surprising, when compared even with the best reducing agent described in the prior art, sodium formate. It has been found that under equivalent conditions, but replacing the formic hydrazide with sodium formate (30% of the weight of bromophthalic acid), using 0.08% of 5% Pd/C as catalyst, the reaction is extremely slow. After 28 hours, 75% of BPTC and 22% of phthalic acid were formed at a 96.6% conversion. Comparison of these data with those of JP 61/137838 shows that with sodium formate as reducing agent the amount of catalyst used has a marked effect not only on the reaction rate but also on the selectivity. With formic hydrazide, this effect is very small (see Table I).

TABLE I

The effect of % catalyst on selectivity and rate of reductive coupling of 4-bromophthalic acid using formic hydrazide as reducing agent (⅔ mole equivalent)

| % Catalyst (based on bromophthalic acid) | % Coupling | Reaction Time (min.) |
|---|---|---|
| 1 | 90 | 15 |
| 0.4 | 89.5 | 30 |
| 0.2 | 89 | 60 |
| 0.08 | 88.3 | 180 |
| 0.04 | 85.3 | 11.5 hours |

Another example of the advantages offered by this application is the reductive coupling of p-bromophenol. Busch et al. obtained 13.4% of biphenol, compared with 80% of biphenol using formic hydrazide and using a commercially available 5% Pd/BaSO$_4$.

DETAILED DESCRIPTION OF THE INVENTION

The following examples are provided to further illustrate the invention, but are not intended to limit its scope in any way.

In the following examples HPLC analyses were carried out using a 10 mm Econosil C-18, 250×4.6 mm column. The mobile phase was 37% Acetonitrile (HPLC grade) and 63% 0.005M Tetrabutyl Ammonium Bromide (TBAB). The pH was 3.1. The flow rate was 2 ml/min., at ambient temperature. The wavelength employed was 230 mm, the injection volume 10 μl, and the concentration was 1.0 mg/ml in Acetonitrile/water 1:1 solution.

The following retention times were obtained.
2.41 min—Phthalic Acid
3.08 min—BPTC 5.57 min—4-Bromophthalic Acid
13.19 min—Dibromophthalic Acid GC analyses were carried out with an SP-2250-3F column:
Detectors temp.: 250° C.
Inject. temp.: 260° C.
Oven temp.: 90° C.
Initial temp.: 50° C.

Temp. rate: 10° C./min; Final temp.: 250° C.

EXAMPLE 1

A 5% Pd/C catalyst (Johnson and Matthey Type 87G) (0.1 g) was added to a warm (40° C.) solution of sodium hydroxide (1.4 g; 35 mmol) in water (10 mL). After stirring for 5 minutes, formic hydrazide, FH (0.4 g; 6.7 mmol) was added and the mixture was stirred for an additional 10 minutes. 4-Bromophthalic acid, 4-BrPA (2.47 g; 10 mmol) was added in one portion; a spontaneous temperature rise to 50°-55° C. was noted.

After stirring for two minutes the mixture was heated to 85° C. and kept at this temperature for 30 minutes. At this stage, an HPLC analysis showed the following composition:
phthalic acid—6.6%
BPTC—93.4%

The catalyst was recovered by filtration at 80° C. The catalyst cake was washed with water (5 mL). The combined filtrates and washings was acidified to pH<1 with 32% HCl (ca. 5 mL). The precipitate which formed was filtered out at 60° C. and washed with water (ca. 100 mL) until the pH of the washings rose to 5-6. The yield of BPTC was 85%-86% and the purity of the product was >99%, as determined by calibrated HPLC.

EXAMPLES 2-8

Example 1 was repeated, using various reaction conditions. The conditions and results are shown in Table II.

EXAMPLES 9-21

Several different starting materials were coupled similarly to Example 1. The starting materials and reaction conditions are detailed in Table III.

TABLE II

| Example | 4-BrPA g | 4-BrPA mol | FH g | FH mol | Pd/C (5%) gr | NaOH mol | H$_2$O ml | time hours | BPTC HPLC area % |
|---|---|---|---|---|---|---|---|---|---|
| 2 | 2.47 | 0.01 | 0.17 | 0.0028 | 0.005 | 0.035 | 20 | 0.3 | 93 |
| 3 | 49 | 0.2 | 8 | 0.134 | 0.1 | 0.75 | 100 | 1 | 89.6 |
| 4 | 49 | 0.2 | 8 | 0.134 | 0.004 | 0.75 | 100 | 3 | 88.7 |
| 5** | 73.5 | 0.3 | 12 | 0.2 | 0.06 | 0.125 | 600 | 12 | 86 |
| 6** | 24.5 | 0.1 | 4 | 0.067 | 0.05 | 0.375 | 200 | 3¼ | 88 |
| 7** | 24.5 | 0.1 | 4 | 0.067 | 0.05 | 0.375 | 200 | 3 | 88.7 |
| 8 | 2.47 | 0.01 | 0.4 | 0.0067 | 0.1 | 0.041* | 10 | 1 | 90.5 |

*KOH was used instead of NaOH
**Examples 5, 6 and 7 used the same recycled catalyst.

TABLE III

| Ex. No. | Substrate Br—Ar | Weight g | Mmol | H$_2$O ml | NaOH g | 5% Pd/C g | Formic Hydrazide g | Temp °C | Time hrs | Analysis Ar—Ar | Product |
|---|---|---|---|---|---|---|---|---|---|---|---|
| 9 | 4-bromoanisole | 9.35 | 50 | 100 | 4 | 0.5 | 2 | 95 | 2 | 86.6 (1) | 4,4'-dianisyl |
| 10 | 4-bromotoluene | 8.55 | 50 | 100 | 4 | 0.5 | 2 | 95 | 2 | 97.3 (1) | 4,4'-ditolyl |
| 11 | 4-bromobenzoic acid | 2.01 | 10 | 20 | 1 | 0.1 | 0.4 | 85 | 1 | 63.7 (2) | 4,4'-biphenyl dicarboxylic acid |
| 12 | 3-bromobenzoic acid | 2.01 | 10 | 20 | 1 | 0.1 | 0.4 | 85 | 1 | 87.7 (2) | 3,3'-biphenyl dicarboxylic acid |
| 13 | 3-bromothiophene | 1.64 | 10 | 25 | 0.8 | 0.1 | 0.4 | 95 | 6 | 67.3 (1) | 3,3'-dithiophene |
| 14 | 4-bromophenyl isopropyl ether | 2.15 | 10 | 20 | 1 | 0.1 | 0.4 | 95 | 4 | 77.7 (1) | 4,4'-bis(isopropoxy) biphenyl |
| 15 | 6-bromo-2-naphthol | 2.23 | 10 | 20 | 1.3 | 0.8 | 0.4 | 80 | 3 | 62.6 (2) | 2,2'-dihydroxy-6,6'-dinaphthyl |
| 16 | 4-bromophenol | 15 |  | 150 | 1.25 | 6 g* | 3 | 80 | 3 | 79 (1) | 4,4'-biphenol |
| 17 | 4(4-bromo-phenoxy phthalic acid | 1.69 | 0.0005 | 15 | 0.68 | 10 mg | 0.2 | 80 | 3 | 92.2 (2) | 4,4'-bis(3'',4''-dicarboxy phenoxy)biphenyl |
| 18 | chlorobenzene | 1.125 | 10 | 20 | 0.8 | 0.05 | 0.4 | 90 | 15 | 53.9 (1) | biphenyl |
| 19 | 4-chlorotoluene (98%; Janssen) | 12.66 | 100 | 200 | 8 | 0.5 | 4 | 80 | 14 | 58.6 (1) | 4,4'-ditolyl |
| 20 | 4-chlorobenzonitrile (98%, Merck) | 1.375 | 10 | 20 | 0.8 | 0.055 | 0.4 | 85 | 1 | 85.7 (1) | 4,4'-dicyanobiphenyl |
| 21 | 4-chlorophthalic acid | 2 | 10 | 20 | 1.5 | 0.02 | 0.4 | 80–85 | 1 | 51.6 (1) | BPTC |
| 22 | 4-[4'-Bromophenyl] phenol | 62.2 | 250 | 170 | 100(3) | 2 | 10 | 70 | 1 | 75.3 | 4,4'''-dihydroxy quaterphenyl |
| 23 | 4-bromo-2,6'-dimethyl phenol | 2 | 10 | 7 | 4(4) | 0.1 | 0.36 | 70 | 2 | 86.2 | 4,4'''-dihydroxy 2,3,2',3' tetramethyl biphenyl |

(1) GC analysis
(2) HPLC Analysis
(3) Na$_2$CO$_3$ was used instead of NaOH - 500 ml of methanol were added
(4) Na$_2$CO$_3$ was used instead of NaOH - 21 ml of methanol were added
*5% Pd/BaSO$_4$ (ex Engelhart)

I claim

1. A method for the preparation of biaryl derivatives wherein an aryl halide is reductively coupled in an aqueous alkaline solution in the presence of a palladium catalyst, using formic hydrazide as the reducing agent.

2. A method according to claim 1, wherein the reaction is carried out at a temperature between 60°–100° C.

3. A method according to claim 1, wherein the catalyst is a supported palladium catalyst.

4. A method according to claim 3, wherein the catalyst is selected from the group consisting of Pd/C and Pd/BaSO$_4$.

5. A method according to claim 1, wherein the molar ratio of formic hydrazide to the halide is about 1:4.

6. A method according to claim 1, wherein the amount of catalyst used is between 0.04% to 4% of the weight of the aryl halide used.

7. A method according to claim 1 wherein the alkali is used in excess of the amount required to neutralize acidic groups and hydrogen halides which are liberated in the reaction mixture and/or produced during the process.

8. A method according to claim 2 wherein the reaction is carried out at a temperature between 60°–85° C.

9. A method according to claim 2, wherein the catalyst is a supported palladium catalyst.

10. A method according to claim 4, wherein the molar ratio of formic hydrazide to the halide is about 1:4.

11. A method according to claim 5, wherein the amount of catalyst used is between 0.04% to 4% of the weight of the aryl halide used.

12. A method according to claim 6, wherein the amount of catalyst used is between 0.08 to 1% of the weight of the aryl halide used.

13. A method according to claim 6, wherein the alkali is used in excess of the amount required to neutralize acidic groups and hydrogen halides which are liberated in the reaction mixture and/or produced during the process.

14. A method according to claim 1, wherein the aryl halide is selected from the group consisting of 4-bromophthalic acid, 4(4'-bromophenoxy) phthalic acid, 4(4'-bromophenyl) phenol, and 4-bromo-2,6-dimethyl phenol.

15. A method according to claim 2, wherein the aryl halide is selected from the group consisting of 4-bromophthalic acid, 4(4'-bromophenoxy) phthalic acid, 4(4'-bromophenyl) phenol, and 4-bromo-2,6-dimethyl phenol.

16. A method according to claim 3, wherein the aryl halide is selected from the group consisting of 4-bromophthalic acid, 4(4'-bromophenoxy) phthalic acid, 4(4'-bromophenyl) phenol, and 4-bromo-2,6-dimethyl phenol.

17. A method according to claim 4, wherein the aryl halide is selected from the group consisting of 4-bromophthalic acid, 4(4'-bromophenoxy) phthalic acid, 4(4'-bromophenyl) phenol, and 4-bromo-2,6-dimethyl phenol.

18. A method according to claim 5, wherein the aryl halide is selected from the group consisting of 4-bromophthalic acid, 4(4'-bromophenoxy) phthalic acid, 4(4'-bromophenyl) phenol, and 4-bromo-2,6-dimethyl phenol.

19. A method according to claim 6, wherein the aryl halide is selected from the group consisting of 4-bromophthalic acid, 4(4'-bromophenoxy) phthalic acid, 4(4'-bromophenyl) phenol, and 4-bromo-2,6-dimethyl phenol.

20. A method according to claim 7, wherein the aryl halide is selected from the group consisting of 4-bromophthalic acid, 4(4'-bromophenoxy) phthalic acid, 4(4'-bromophenyl) phenol, and 4-bromo-2,6-dimethyl phenol.

* * * * *